(12) United States Patent
Van Tol et al.

(10) Patent No.: US 6,723,806 B2
(45) Date of Patent: Apr. 20, 2004

(54) METAL COMPLEX CONTAINING ONE OR MORE SILSESQUIOXANE LIGANDS

(75) Inventors: Maurits F. H. Van Tol, Limbricht (NL); Sven K. H. Thiele, Alsdorf (DE); Robbert Duchateau, Eindhoven (NL); Hendrikus C. L. Abbenhuis, Breda (NL); Rutger A. Van Santen, Eindhoven (NL)

(73) Assignee: DSM N.V., Heerlen (NL)

( * ) Notice: Subject to any disclaimer, the term of this patent is extended or adjusted under 35 U.S.C. 154(b) by 143 days.

(21) Appl. No.: 09/740,037

(22) Filed: Dec. 20, 2000

(65) Prior Publication Data

US 2001/0008926 A1 Jul. 19, 2001

Related U.S. Application Data

(63) Continuation of application No. PCT/NL99/00397, filed on Jun. 28, 1999.

(30) Foreign Application Priority Data

Jun. 26, 1998 (EP) .............................................. 98202140

(51) Int. Cl.$^7$ .............................. C08F 4/76; C08F 4/74; C07F 7/18; C07F 7/28; C07F 19/00
(52) U.S. Cl. ........................ 526/113; 526/114; 526/133; 526/134; 502/158; 556/10
(58) Field of Search ................................. 526/113, 114, 526/133, 134; 502/158; 556/10

(56) References Cited

FOREIGN PATENT DOCUMENTS

DE 19715786 A1 * 10/1998

OTHER PUBLICATIONS

Duchateau et al., "Half–Sandwich Titanium Complexes Stabilized by a Novel Silsesquioxane Ligand: Soluble Model Systems for Silica–Grafted Olefin Polymerization Catalysts", *Organometallics*, 1998, 17, 522205224.

Buys et al., "Models of surface–confined metallocene derivatives", Journal of Molecular Catalysis, vol. 86, No. 1/03, 1994, pp 309–318.

Feher et al., "Olefin polymerization by vanadium–containing polyhedral oligometallasilsesquioxanes", Journal of the American Chemical Society, vol. 113, 1991, pp 3618–3619.

Feher et al., "Silasesquioxanes as ligands in inorganic and organometallic chemistry", Polyhedron, vol. 14, No. 22, Oct. 1995, pp. 3239–3253.

Duchateau et al., "Ethylene polymerization with dimeric zirconium and hafnium silsesquioxan complexes", Organometallics, 1998, 17(26), pp 5663–5673.

* cited by examiner

*Primary Examiner*—Caixia Lu
(74) *Attorney, Agent, or Firm*—Pillsbury Winthrop LLP

(57) ABSTRACT

Metal complex containing one or more silsesquioxane ligands having the formula:

$$Z_y(MA_x)_b \qquad (I)$$

wherein

Z is a silsesquioxane ligand according to the formula:

$$(RSiO_{1.5})_m O_n B_q \qquad (II)$$

which is connected within one corner to one atom M or to two atoms M by one bridging oxygen atom, M is a metal from groups 3–10 of the Periodic System of the Elements and the lanthanides, A is a substituent bonded to the metal, y represents the number of silsesquioxane ligands and is 2–10, b represents the number of metal groups and is 2–20, x is the number of substituents A bonded to the metal; the value of x depends on the metal used and is equal to the valency of the metal minus 1, 2, 3 or 4, R is a substituent bonded to each Si, m is an integer and is equal to 5–19, n is 1.5 or 3, B is a group bonded to an oxygen atom that has one bond to Si and q is 0, 1 or 2.

12 Claims, No Drawings

METAL COMPLEX CONTAINING ONE OR MORE SILSESQUIOXANE LIGANDS

This is a Continuation of: International Appln. No. PCT/NL99/00397 filed Jun. 28, 1999 which designated the U.S., and that International Application was published under PCT Article 21(2) in English.

The invention is related to a metal complex containing one or more silsesquioxane ligands. Metal complexes containing one or more silsesquioxane ligands are for instance known from FEHER F. J. et al., 'Olefin Polymerization by Vanadium-Containing Polyhedral Oligometallasilsesquioxanes', J. Am. Chem. Soc., 1991, 113, p. 3618–3619.

In this article a vanadium complex is described containing one silsesquioxane ligand. It is reported that this complex is active in the polymerisation of ethylene when it is activated with an aluminum containing co-catalyst.

In this article it is also reported that a metal complex containing two vanadium atoms and two silsesquioxane ligands is not active in the polymerisation of ethylene.

It is now surprisingly discovered that a metal complex with the formula $$Z_y(MA_x)_b \quad (I)$$

wherein Z is a silsesquioxane ligand according to the formula $$(RSiO_{1.5})_mO_nB_q \quad (II)$$

which is connected within one corner to one atom M or to two M atoms by one bridging oxygen atom.

M is a metal from groups 3–10 of the Periodic System of the Elements and the lanthanides, A is a ligand bonded to the metal, y represents the number of silsesquioxane ligands and is 2–10, b represents the number of metal groups and is 2–20, x is the number of ligands A bonded to the metal; the value of depends on the metal used and is equal to the valency of the metal minus 1, 2, 3 or 4, R is a substituent bonded to each Si, m is an integer and is equal to 5–19, n is 1.5 or 3, B is a group bonded to an oxygen atom that has one bond to Si and q is 0, 1 or 2 is active in the polymerisation of olefins.

A further advantage of the metal complex according to the invention is that polyolefins having a narrow molecular weight distribution can be produced by using these metal complexes.

Other advantages of the metal complex according to the invention are that the metal complex is active in the polymerisation of olefins even without the presence of a cocatalyst and that the metal complexes supported on a carrier material are active in the polymerisation of olefins without the presence of a scavenger.

In the following the various components of the metal complex according to the invention will be discussed in more detail.

a) The silsesquioxane ligand Z

The silsesquioxane ligand Z is a ligand according to the formula $$(RSiO_{1.5})_mO_nB_q \quad (II)$$

wherein

R is a substituent bonded to each Si, m is an integer and is equal to each Si, n is 1.5 or 3, B is a group bonded to an oxygen atom that has one bond to Si and q is 0, 1 or 2.

The silsesquioxane has a cubic or prismatic (trigonal, hexagonal or pentagonal) structure with a Si atom at each corner and oxygen atoms connecting the Si atoms. The silsesquioxane can, for example, be represented by the following structures:

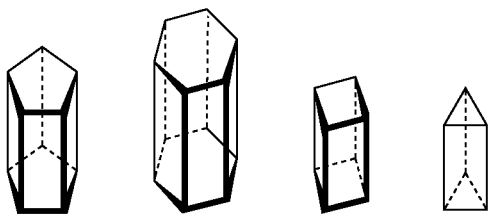

In the silsesquioxane ligands 1 or 2 of the Si-atoms are not present so that it is at this place bonded to the metal atom or atoms. This place is defined as a "corner". It is bonded to a metal atom via at least one oxygen atom. In the silsesquioxane ligand, the Si-atom is not present at one or two of the corners of the silsesquioxane polygonal structure. A Si absent corner is defined as the "corner". The "corner" is bonded to a metal atom via at least one oxygen atom. The oxygen atoms that are not involved in bonding with the metal atom(s) are bonded to a group B. The B groups can be the same or different and can for instance be hydrogen or an alkyl, aryl, silyl, germyl or stannyl group. The silsesquioxane ligands are connected within one corner to one atom M or to two atoms M by one bridging oxygen atom. In the metal complex according to formula I, $Z_y(MA_x)_b$, y is in the range 2–10, i.e. 2–10 silsesquioxane ligands can be present. In the metal complex according to the invention 2–10 silsesquioxane ligands can be present (represented by y in formula I).

R is a substituent bonded to each Si of the silsesquioxane ligand Z.

The R groups can be the same or different and can for instance be hydrogen or an alkyl, aryl or silyl group. R is preferably cyclopentyl, cyclohexyl, cycloheptyl or hydrogen.

Preferably the metal complex according to the invention contains silsesquioxane ligands according to the formulas $$(RSiO_{1.5})_7O_{1.5}, (RSiO_{1.5})_7O_{1.5}B \text{ or } (RSiO_{1.5})_7O_{1.5}B_2$$

wherein R is a substituent bonded to each Si and B is a group bonded to an oxygen atom that has one bond to Si. More preferably the metal complex according to the invention contains silsesquioxane ligands according to the formula $$(RSiO_{1.5})_7O_{1.5}$$

The silsesquioxane ligands mentioned above are represented by the following structures

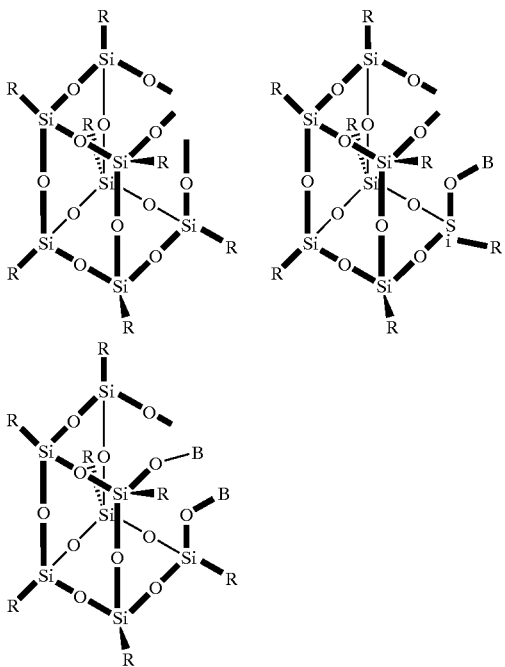

b) The metal M

The metals in the complex are chosen from groups 3–10 of the Periodic Table of the Elements and the lanthanides (see the new IUPAC notation to be found on the inside of the cover of the Handbook of Chemistry and Physics, 70th edition, 1989/1990). The metal atoms present in the metal complex according to the invention can be the same or different. In the metal complex according to formula I, $Z_y(MA_x)_b$, b is in the range 2–20, i.e. 2–20 metal atoms can be present. M is preferably chosen from groups 3–6 of the Periodic Table of the Elements. More preferably M is a metal out of group 4 of the Periodic Table of the Elements.

c) The ligand A

The ligand A is bonded to the metal. The ligands A can be the same or different and can, for example, be a hydrocarbon substituent containing 1–20 carbon atoms (such as alkyl, aryl, aralkyl, and the like). Examples of such hydrocarbon substituents are methyl, ethyl, propyl, butyl, hexyl, decyl, phenyl, benzyl, and p-tolyl. Ligand A may also be a ligand which in addition to, or instead of, carbon and/or hydrogen, contains one or more hetero atoms from groups 14–17 of the Periodic System of the Elements, a hetero atom not being bound directly to a cyclopentadienyl (Cp) group. Thus a ligand A may be an N-, O-, and Cl-, or Si-containing group. Examples of ligands containing a hetero atom are alkoxy, aryloxy or dialkyl amido groups.

A is preferably an alkyl- or aryl group. The number of ligands A (represented by x in formula I) depends on the metal used and is equal to the valency of the metal minus 1, 2, 3 or 4. When the silsesquioxane ligand is bound to the metal with 3 oxygen atoms the number of ligands A on the metal is equal to the valency of the metal minus 3. When the silsesquioxane ligand is bound to the metal with 2 oxygen atoms the number of ligands A on the metal is equal to the valency of the metal minus 2. When the silsesquioxane ligand is bound to the metal with 1 oxygen atom the number of ligands A on the metal is equal to the valency of the metal minus 1.

Preferably the metal complex according to the invention is a bimetallic complex according to the formulas

or

wherein M, A, Z and x have the meaning as defined above.

Most preferably the metal complex according to the invention is a bimetallic complex according to formula wherein M, A, Z and x have the meaning as defined above.

Within these metal complexes the metals and the silsesquioxane ligands can be bound to each other in several ways. Examples of possible bonding structures are given below. In these structures only a part of the whole silsesquioxane ligand is shown. The rest of the ligand is mentioned Z*.

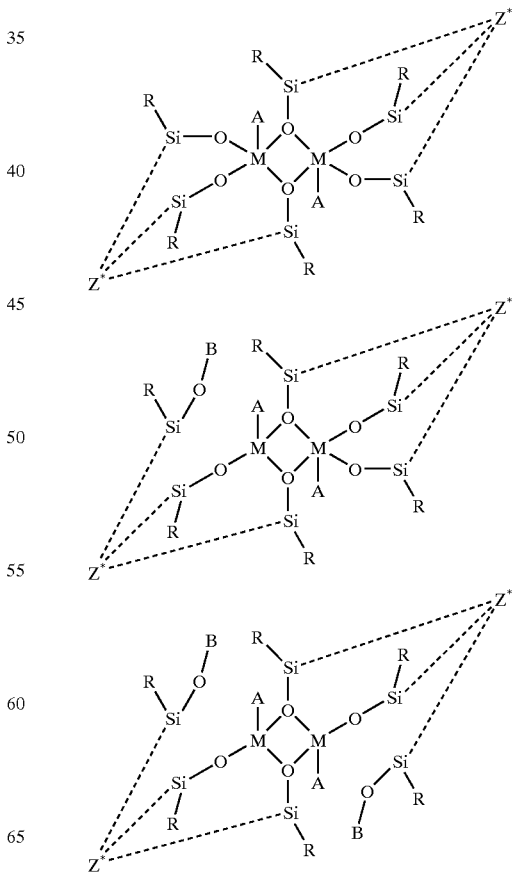

-continued

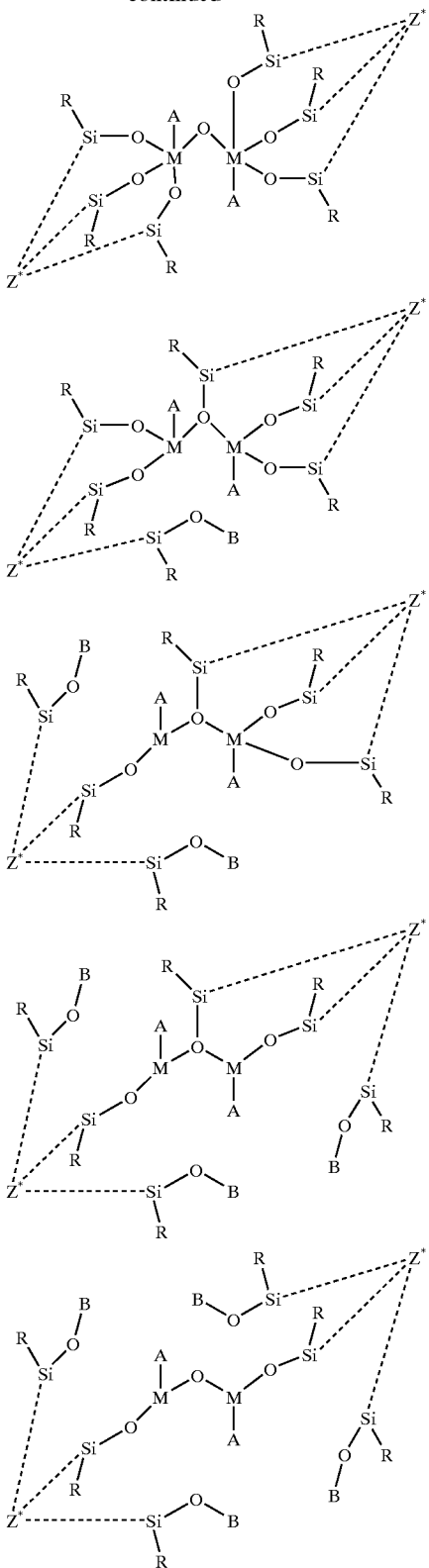

The metal complex according to the invention can be supported on a carrier material. Examples of suitable carrier materials are any finely divided solid porous support material, including, but not limited to, $MgCl_2$, Zeolites, mineral clays, inorganic oxides such as, for instance, talc, silica, alumina, silica-alumina, meso-porous silica, meso-porous alumosilica, meso-porous alumophospates, inorganic hydroxides, phosphates, sulphates, or resinous support materials such as polyolefins, including polystyrene, or mixtures thereof. These carriers may be used as such or modified, for example by silanes and/or aluminium alkyles and/or aluminoxane compounds. Preferably the carrier material has a specific surface area of at least 10 $m^2$ per gram and a pore volume of at least 0.1 ml per gram.

Most preferably the carrier material is silica or meso-porous silica. More preferably dehydrated or modified silica such as silylated silica is the carrier material. The silica carrier material can also be modified with a co-catalyst; for instance methyl aluminoxane.

The silsesquioxane ligands are generally prepared by addition of excess water to a vigorously stirred solution of the appropriate trichlorosilane, $RSiCl_3$, in an organic solvent. This is, for instance, described in FEHER R. J. et al., J. Am. Chem. Soc., 111 (1989), p. 1741–1748.

The metal complex according to the invention can be prepared by reacting 1 to 5 equivalents of a ligand with the formula:

$$(RSiO_{1.5})_m O_n B_q H_p \qquad (III)$$

with 1 to 2 equivalents of a metal complex $MA_xX_c$ wherein the symbols have the meaning as defined above and X is a monoanionic ligand that is able to react with an OH-group, p is 1–4 and c is 1–4. The monoanionic ligand X can be can be the same or different and can, for example, be a hydrocarbon radical containing 1–20 carbon atoms (such as alkyl, aryl, aralkyl, and the like). Examples of such hydrocarbon radicals are methyl, ethyl, propyl, butyl, hexyl, decyl, phenyl, benzyl, and p-tolyl. X can also be an halide, sulfide or dialkyl amido ligand. The ligands A on the metal can be the same as the ligands X. The metal complexes according to the formulas:

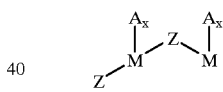

and

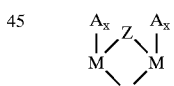

can be prepared by stirring a metal compound $MA_xX_c$ with of the silsesquioxane ligand in an aprotic organic solvent in which the reactants are sufficiently soluble. Suitable solvents are apolar non-coordinating solvents such as pentane, toluene and dichloromethane. The reaction is preferably performed under an inert gas (e.g., nitrogen or argon). Generally the reaction is performed at room temperature and with a pressure about atmospheric pressure. The reaction is generally completed within a few minutes.

The concentration of the reactants is not of primary importance, but convenient concentrations are in the region of 0.001–0.1 M for each reactant. Isolation of the metal complex is normally accomplished by removing the volatile material present (i.e. solvent and reaction side-product) under reduced pressure, by precipitation or by crystallisation.

Supported catalyst systems of the invention may be prepared by several methods. The metal complex and eventually the co-catalyst can be mixed together before the addition of the support material. The mixture may be prepared in conventional solution in a normally liquid alkane or aromatic solvent. The solvent is preferably also suitable for use as a polymerization diluent for the liquid phase polymerization of an olefin monomer. Alternatively, the co-catalyst can be placed on the support material followed by the addition of the metal complex or conversely, the metal complex may be applied to the support material followed by the addition of the co-catalyst. The co-catalyst can be used as commercially supplied, or may be generated in situ on the solid support. The supported catalyst may be prepolymerized. In addition third components can be added in any stage of the preparation of the supported catalyst. Third components can be defined as compounds containing Lewis acidic or basic functionalities exemplified but not limited to compounds such as N,N-dimethylaniline, tetraethoxysilane, phenyltriethoxysilane, bis-tert-butylhydroxy toluene (BHT) and the like.

The solid-phase immobilization (SPI) technique described by H. C. L. Abbenhuis in *Angew. Chem. Int. Ed.* 37 (1998) 356–58, by M. Buisio et al. in *Microporous Mater.*, 5 (1995) 211 and by J. S. Beck et al. in *J. Am. Chem. Soc.*, 114 (1992) 10834 as well as the pore volume impregnation (PVI) technique (see WO 97/24344) can be used to support the metal complex on to the carrier material. The isolation of the impregnated carrier can be done by filtration or by removing the volatile material present (i.e. solvent) under reduced pressure.

The metal complex according to the invention can be used, without activation with a co-catalyst, for the polymerisation of olefins. The metal complex can also be activated using a co-catalyst. The activation can be performed during a separate reaction step including an isolation of the activated compound or can be performed in situ. The activation is preferably performed in situ, because after the activation of the metal complex separation and/or purification of the activated complex is not necessary.

The metal complexes according to the invention can be activated using suitable co-catalysts. For example, the co-catalyst can be an organometallic compound, wherein at least one hydrocarbon radical is bonded directly to the metal to provide a carbon-metal bond. The hydrocarbon group used in the organometallic compounds preferably contains 1–30, more preferably 1–10 carbon atoms. The metal of the organometallic compound can be selected from group 1, 2, 3, 12, 13 or 14 of the Periodic Table of the Elements. Suitable metals are, for example, sodium, lithium, zinc, magnesium and aluminium and boron.

Examples of suitable co-catalysts are alkyl sodium, alkyl lithium, alkyl zinc, alkyl magnesium halide, dialkyl magnesium, organoaluminum compounds and halogen-containing organoaluminum compounds. Examples of organoaluminum compounds are triaryl and trialkyl aluminum compounds, such as triethyl aluminum and triisobutyl-aluminum; alkyl aluminum hydrides, such as diisobutyl aluminum hydride; alkylalkoxy organoaluminum compounds; and halogen-containing organoaluminum compounds, such as diethyl aluminum chloride, diisobutyl aluminum chloride and ethyl aluminum sesquichloride. Linear or cyclic aluminoxanes can also be used as co-catalyst.

The metal complex according to the invention can also be activated with a compound which contains or yields in a reaction with the metal complex of the present invention a non-coordinating or poorly coordinating anion. Such compounds have been described for instance in EP-A-426,637, the complete disclosure of which is incorporated herein by reference. Such an anion is bonded sufficiently unstable such that it is replaced by an unsaturated monomer during the polymerization. Such compounds are also mentioned in EP-A-277,003 and EP-A-277,004, the complete disclosures of which are incorporated herein by reference. Such a compound preferably contains a triaryl borane or a tetraaryl borate or an aluminum equivalent thereof. Examples of suitable co-catalyst compounds include, without limitation, the following:

dimethyl anilinium tetrakis (pentafluorophenyl) borate $[C_6H_5N(CH_3)_2H]^+ [B(C_6F_5)_4]^-$;

dimethyl anilinium bis(7,8-dicarbundecaborate) cobaltate (III);

tri(n-butyl)ammonium tetraphenyl borate;

triphenylcarbenium tetrakis (pentafluorophenyl) borate;

tetrakis (3,5-bistrifluoromethyl-phenyl) borate;

dimethylamilinium tetraphenyl borate;

tris(pentafluorophenyl) borane and tris[3,5-bis(trifluormethyl)]borane.

If the above-mentioned non-coordinating or poorly coordinating anion is used as the co-catalyst, it is preferable for the metal compound according to the invention to be alkylated (that is, one of the A groups is an alkyl or aryl group). Co-catalysts containing boron are preferred. Most preferred are co-catalysts containing tetrakis(pentafluorophenyl) borate, tris(pentafluorophenyl)borane, or tetrakis(3,5-bistrifluoromethyl-phenyl)borate.

When a boron containing co-catalyst is used the polymerisation time is longer than when an other co-catalyst is used for the homogeneous polymerisation of olefins.

The molar ratio of the co-catalyst relative to the metal center in the metal complex in case an organometallic compound is selected as the co-catalyst, usually is in a range of from about 1:10 to about 10,000:1, and preferably is in a range of from about 1:1 to about 2,500:1. If a compound containing or yielding a non-coordinating or poorly coordinating anion is selected as co-catalyst, the molar ratio usually is in a range of from about 1:100 to about 1,000:1, and preferably is in range of from about 1:2 to about 250:1.

In addition to the metal complex according to the invention and the co-catalyst the catalyst composition can also contain a small amount of an other organometallic compound that is used as a so called scavenger. The scavenger is added to react with impurities in the reaction mixture. It is normally added to the reaction mixture before addition of the metal complex and the co-catalyst. Usually organoaluminum compounds are used as a scavenger. Examples of scavengers are trioctylaluminium, triethylaluminium and tri-isobutylaluminium.

As a person skilled in the art would be aware, the metal complex as well as the co-catalyst can be present in the catalyst composition as a single component or as a mixture of several components. For instance, a mixture may be desired where there is a need to influence the molecular properties of the polymer, such as molecular weight distribution.

The metal complex according to the invention can be used for the polymerization of olefin monomers. The olefin envisaged in particular is an olefin chosen from the group comprising α-olefin, internal olefin, cyclic olefin and di-olefin. Mixtures of these can also be used.

The metal complex according to the invention is in particular suitable for a process for the polymerization of an α-olefin. In particular the α-olefin monomer(s) is/are chosen from the group comprising ethene, propene, butene, pentene, heptene, hexene and octene (substituted or non-substituted), mixtures of which may also be used. More preferably, ethene and/or propene is used as a-olefin. The use of such olefins results in the formation of (semi)crystalline polyethene homo- and copolymers, of high as well as of low density (HDPE, LDPE, LLDPE, etc.), and polypropene, homo- and copolymers (PP and EMPP). The monomers needed for such products and the processes to be used are known to the person skilled in the art.

With the metal complex according to the invention amorphous or rubber-like copolymers based on ethene and another α-olefin can also be prepared. Propene is preferably used as the other α-olefin, so that EPM rubber is formed. It is also quite possible to use a diene besides ethene and the other α-olefin, so that a so-called EADM rubber is formed, in particular EPDM (ethene propene diene rubber).

Polymerization of the α-olefin monomer(s) can be effected in a known manner, in the gas phase as well as in a liquid reaction medium. In the latter case, both solution and suspension polymerization are suitable. The supported catalyst systems according to the invention are used mainly in gas phase and slurry processes. The quantity of metal to be used generally is such that its concentration in the dispersion agent amounts to $10^{-8}$–$10^{-3}$ mol/l, preferably $10^{-7}$–$10^{-4}$ mol/l.

The invention will hereafter be elucidated with reference to polymerisations of α-olefins known per se, which are representative of the polymerization referred to in the present description. For the preparation of other polymers on the basis of α-olefin monomers the reader is expressly referred to the multitude of publications on this subject.

The polymerisation process can be conducted as a gas phase polymerisation (e.g. in a fluidized bed reactor), as suspension/slurry polymerisation, as a solid phase powder polymerisation or as a so called bulk polymerisation process, in excess of olefinic monomer used as the reaction medium. Dispersion agents may suitably be used for the polymerisation, which may in particular, but not limited to, be chosen from saturated, straight or branched aliphatic hydrocarbons, such as butanes, pentanes, hexanes, heptanes, pentamethyl heptane or mineral oil fractions such as light or regular petrol, naphtha, kerosine or gas oil. Also fluorinated hydrocarbons or similar liquids are suitable for that purpose. Aromatic hydrocarbons, for instance benzene and toluene, can be used, but because of their cost as well as on account of safety considerations, it will be preferred not to use such solvents for production on a technical scale. In polymerization processes on a technical scale, it is preferred therefore to use as solvent the low-priced aliphatic hydrocarbons or mixtures thereof, as marketed by the petrochemical industry. If an aliphatic hydrocarbon is used as solvent, the solvent may yet contain minor quantities of aromatic hydrocarbon, for instance toluene. Thus, if for instance methyl aluminoxane (MAO) is used as co-catalyst, toluene can be used as solvent for the MAO in order to supply the MAO in dissolved form to the polymerization reactor. Drying or purification of the solvents is desirable if such solvents are used; this can be done without problems by the average person skilled in the art.

In the polymerisation process the metal complex and the co-catalyst are used in a catalytically effective amount, i.e. any amount that succesfully results in the formation of polymer. Such amounts may be readily determined by routine experimentation by the skilled art worker.

Those skilled in the art will easily understand that the catalyst systems used in accordance with this invention may also be prepared in-situ.

If a solution or bulk polymerisation is to be used it is preferably carried out at temperatures well above the melting point of the polymer to be produced, typically, but not limited to, temperatures between 120° C. and 260° C.

The polymerisation process can also be carried out under suspension or gasphase polymerization conditions which typically take place at temperatures well below the melting temperature of the polymer to be produced, typically, but not limited to, temperatures below 105° C.

The polymer resulting from the polymerization can be worked up by a method known per se. In general the catalyst is de-activated at some point during the processing of the polymer. The de-activation is also effected in a manner known per se, e.g. by means of water or an alcohol. Removal of the catalyst residues can mostly be omitted because the quantity of catalyst in the polymer, in particular the content of halogen and metal is very low now owing to the use of the catalyst system according to the invention.

Polymerization can be effected at atmospheric pressure, at sub-atmospheric pressure, or at elevated pressure of up to 500 MPa, continuously or discontinuously. Preferably, the polymerization is performed at pressures between 0.01 and 500 MPa, most preferably between 0.01 and 10 MPa, in particular between 0.5–3 MPa. Higher pressures can be applied. In such a high-pressure process the metal complex according to the present invention can also be used with good results. Slurry and solution polymerisation normally take place at lower pressures, preferably below 20 MPa.

The polymerization can also be performed in several steps, in series as well as in parallel. If required, the catalyst composition, temperature, hydrogen concentration, pressure, residence time, etc. may be varied from step to step. In this way it is also possible to obtain products with a wide molecular weight distribution.

By using the metal complexes according to the present invention for the polymerisation of olefins polymers are obtained with a polydispersity (Mw/Mn) of 1.5–50. It is an advantage that also polymers with a narrow polydispersity can be produced, i.e polymers with a polydispersity of 1.5–2.5.

The invention also relates to a polyolefin polymer which can be obtained by means of the polymerization process according to the invention.

The invention will now be illustrated by means of the following non-restrictive examples.

EXAMPLES

General

All tests in which organometallic compounds were involved were carried out in an inert nitrogen atmosphere, using standard Schlenk equipment. In the following 'Ph' means 'phenyl'. Pressures mentioned are absolute pressures. The products were characterized by means of SEC-DV (size exclusion chromatography), and NMR with a Bruker ACP 200 ($^1$H=400 MHz; $^{13}$C=100 MHz). Mn and Mw are molecular weights determined by universal calibration of SEC-DV.

A) Preparation of the Catalyst Precursor

Example I

Preparation of $\{[(c\text{-}C_5H_9)_7Si_7O_{12}]ZrCH_2C_6H_5\}_2$ 1

At −80° C., a solution of $Zr(CH_2C_6H_5)_4$ (3.05 g, 6.69 mmol) in toluene (30 mL) was added to a suspension of $(c\text{-}C_5H_9)_7Si_7O_9(OH)_3$ in toluene. The mixture was allowed to warm to room temperature and was subsequently stirred for 1 hour. The volatiles were removed in vacuo and the oily yellow product was stripped with hexanes (1×10 mL). The product was dissolved in hexane (50 mL) and filtered to remove minor amounts of insoluble impurities. Concentration and cooling to −30° C. gave the dimeric {[(c-C$_5$H$_9$)$_7$Si$_7$O$_{12}$]ZrCH$_2$C$_6$H$_5$}$_2$ (5.2 g, 2.47 mmol, 71%) as pale yellow block shaped crystals. $^1$H NMR (Benzene-d$_6$, δ): 7.47 (d, 2H, C$_6$H$_5$, $^3J_{H\text{-}H}$=7 Hz), 7.28 (dd, 2H, C$_6$H$_5$, $^3J_{H\text{-}H}$=7 Hz), 6.99 (d, 1H, C$_6$H$_5$, $^3J_{H\text{-}H}$=7 Hz), 3.12 (s, 2H, CH$_2$C$_6$H$_5$, 1.7 (m, 50H, C$_5$H$_9$), 1.2 (m, 6H, C$_5$H$_9$), 1.1 (m, 4H, C$_5$H$_9$), 0.8 (m, 3H, C$_5$H$_9$). $^{13}$C NMR (Benzene-d$_6$, δ): 142.3 (s, ipso-C$_6$H$_5$), 129.9 (d, C$_6$H$_5$, $^1J_{C\text{-}H}$=160 Hz), 124.7 (d, C$_6$H$_5$, $^1J_{C\text{-}H}$=157 Hz), 57.6 (t, CH$_2$C$_6$H$_5$, $^1J_{C\text{-}H}$=124 Hz), $^{13}$C{$^1$H}: 28.4, 28.1, 27.8, 27.6, 27.5, 27.2, 25.6, 23.6, 23.0, 22.8, 22.6 (s, C$_5$H$_9$). $^{29}$Si{$^H$} NMR (toluene, 213 K, δ): −57.23, −61.48, −62.05, −62.98, −65.14, −65.57, −67.07.

Example II

Preparation of {[(c-C$_5$H$_9$)$_7$Si$_7$O$_{12}$]HfCH$_2$C$_6$H$_5$}$_n$ 2

A solution of Hf(CH$_2$Ph)$_4$ (1.88 g, 3.46 mmol) in toluene (25 mL) was cooled to −50° C. and solid (c-C$_5$H$_9$)$_7$Si$_7$O$_9$(OH)$_3$ (3.03 g, 3.46 mmol) was added. The mixture was warmed to room and stirred overnight. Evaporation of the solvent left a white solid. Crystallization of the product from hexane (10 mL) containing a small amount of ether (0.5 mL) afforded pure {[(c-C$_5$H$_9$)$_7$Si$_7$O$_{12}$]HfCH$_2$C$_6$H$_5$}$_n$ as a white microcrystalline material (1.70 g, 1.49 mmol, 43%). $^1$H NMR (Benzene-d$_6$, δ): 7.43 (d, 2H, o-C$_6$H$_5$, $^3J_{H\text{—}H}$=7 Hz), 7.28 (t, 2H, m-C$_6$H$_5$, $^3J_{H\text{—}H}$=7 Hz), 6.88 (t, 1H, p-C$_6$H$_5$, $^3J_{H\text{—}H}$=7 Hz), 2.62 (s, 2H, HfCH$_2$Ph), 2.0–1.5 (m, broad, 56 H, CH$_2$—C$_5$H$_9$), 1.2 (m, broad, 7H, CH—C$_5$H$_9$). $^{13}$C NMR (Benzene-d$_6$, δ): 148.15 (s, ipso-C$_6$H$_5$), 128.41 (d, C$_6$H$_5$, $^1J_{C\text{—}H}$=160 Hz), 127.97 (d, C$_6$H$_5$, $^1J_{C\text{—}H}$=160 Hz), 122.16 (d, o-C6H$_5$, $^1J_{C\text{-}H}$=157 Hz), 65.30 (t, Hf—CH$_2$, $^1J_{C\text{—}H}$ 112 Hz). $^{13}$C{$^1$H} NMR (Benzene-d$_6$, δ): 28.27, 27.96, 27.76, 27.63, 27.38 (s, CH$_2$—C$_5$H$_9$); 23.58, 22.81, 22.42 (s, 3:3:1, CH—C$_5$H$_9$)

B) Preparation of the Polymerization Catalyst

Example III

Preparation of the Polymerization Catalyst 3

2 ml of a toluene solution containing 2*10$^{-5}$ mol of complex 1 was contacted with 1 ml of a toluene solution containing 2*10$^{-5}$ mol tris-(pentafluorophenyl)borane [B(C$_6$F$_5$)$_3$]. After stirring the solution for 10 minutes the polymerization catalyst 3 was formed. The polymerization catalyst 3 could be stored for weeks, if the toluene solvent was removed.

Example IV

Preparation of the Polymerization Catalyst 4

2 ml of a toluene solution containing 2*10$^{-5}$ mol of complex 2 was contacted with 1 ml of a toluene solution containing 2*10$^{-5}$ mol tris-(pentafluorophenyl)borane [B(C$_6$F$_5$)$_3$]. After stirring the solution for 10 minutes the polymerization catalyst 4 was formed. The polymerization catalyst 4 could be stored for weeks at low temperatures, if the toluene solvent was removed.

C) Preparation of the supported catalyst system

Example V

Preparation of the Supported Polymerization Catalyst 5

1 ml of a toluene solution containing 1*10$^{-5}$ mol of complex 1 was adsorbed on 1 g silica PQ3040 containing MAO (aluminum content of the silica: 0.247 g), stirred for 3 hours and dried in the vacuum.

D) Polymerization Reactions

Example VI

Polymerization Using The Polymerization Catalyst 3

General Procedure:

600 ml of an alkane mixture was brought as solvent under dry nitrogen in a stainless steel reactor having a volume of 1.5 liter. The reactor was than heated under constant mixing to the required temperature under an absolute pressure of ethylene of 5 bar (500 kPa).

In a catalyst dosing vessel having a content of 100 ml, 25 ml of an alkane mixture was dosed as dilution medium. Then, 1 mmol of the scavenger tris-(pentafluorophenyl)borane [B(C$_6$F$_5$)$_3$], dissolved in 10 ml toluene, was added to the reactor. After 15 minutes the desired amount of catalyst was introduced into the same catalyst dosing vessel containing again 25 ml of an alkane mixture. The resulting solution thus obtained was subsequently dosed into the reactor. The polymerization reaction was started and carried out under isothermal conditions. The ethylene pressure was maintained constant at 5 bar absolute. The ethylene addition was interrupted after 7 minutes and the reaction mixture was quenched with methanol. Irganox 1076 (™) was then added to the product as anti-oxidant to stabilize the polymer. The polymer was dried under vacuum at 70° C. for 24 hours. Using this general procedure 2*10$^{-5}$ moles of the polymerization catalyst 3 (see Example III) dissolved in 3 ml toluene were added to the reactor. Three polymerizations were carried out at polymerization temperatures of 30, 50 and 80° C. (see Table 1). The obtained polymer was analysed by SEC-DV (weight-averaged molecular weight (M$_w$) and molecular weight distribution (MWD) see also table 1).

TABLE 1

| | polymerization temperature [° C.] | | |
|---|---|---|---|
| | 30 | 50 | 80 |
| activity [kg (PE)/g (Zr) *7 min] | 5.0 | 2.8 | 1.5 |
| M$_w$ [kg/mol] | 32000 | — | 6600 |
| MWD (M$_w$/M$_n$) | 9.2 | — | 2.3 |

Example VII

Polymerization Using The Polymerization Catalyst 4

Using the general procedure described in Example VI 1 mmol of the scavenger tris-(pentafluorophenyl)borane [B(C$_6$F$_5$)$_3$] dissolved in 10 ml toluene and 2*10$^{-5}$ moles of the polymerization catalyst 4 (see example IV) dissolved in 3 ml toluene were added to the reactor. The polymerization was carried out at a polymerization temperature of 50° C. The obtained polymer (1.6 [kg(PE)/g(Hf)*7 mm]) was analysed by SEC-DV. The weight-averaged molecular weight (M$_w$) was 82000 kg/mol and the molecular weight distribution (MWD) amounts to 3.2.

Example VIII

Polymerization Using The Supported Polymerization Catalyst 5

600 ml of an alkane mixture were brought as solvent under dry nitrogen in a stainless steel reactor having a content of 1.5 liter. The reactor was than heated under constant mixing to the required temperature under an absolute pressure of ethylene of 5 bar (500 kPa).

In a catalyst dosing vessel having a content of 100 ml, 25 ml of an alkane mixture was dosed as dilution medium. Then, the supported polymerization catalyst 5 (see example V) was introduced into the same catalyst dosing vessel containing 25 ml of an alkane mixture. The resulting mixture thus obtained was subsequently dosed into the reactor. The polymerization reaction was thus started and carried out under isotherm conditions at 29° C. without any further use of scavanger. The ethylene pressure was maintained constant at 5 bar absolute. The ethylene addition was interrupted after 7 minutes and the reaction mixture was collected and quenched with methanol. Irganox 1076 (™) was then added to the product as anti-oxidant to stabilize the polymer. The polymer was dried under vacuum at 70° C. for 24 hours. The obtained polymer (3.2 [kg(PE)/g(Zr)*7 min]) was analysed by SEC-DV. The weight-averaged molecular weight ($M_w$) was 65000 kg/mol and the molecular weight distribution (MWD) amounts to 11.7.

What is claimed is:

1. Process for the polymerization of olefins, comprising contacting the olefin with a metal complex having the formula $Z_y(MA_x)_b$, wherein Z is a silsesquioxane ligand of formula (II):

$$(RSiO_{1.5})_mO_nB_q \qquad (II)$$

and is connected wish one corner where a Si-atom is not present to two M atoms by one bridging oxygen atom, wherein the bridging oxygen atom is from the silsesquioxane or formula (II), M is a metal from groups 3–10 of the Periodic System of the Elements and the lanthanides, A is a hydrocarbon substitutent containing 1–20 carbon atoms covalently bonded to the metal, y represents the number of silsesquioxane ligands and is 2–10, b represents the number of metal groups and is 2–20, x is the number of substituents A bonded to the metal, the value of x depending on the metal used and is equal to the valency of the metal minus 1, 2, 3 or 4, R is a substituent bonded to each Si, m is an integer and is equal to 5–19, q is 1, 5 or 3, B is a group bonded to an oxygen atom that has one bond to Si, and q is 0, 1 or 2.

2. Process according to claim 1, wherein a co-catalyst is present during the polymerization.

3. Process according to claim 2, wherein the co-catalyst comprises a boron containing co-catalyst.

4. Process according to claim 3, wherein the boron co-catalyst contains tetrakis(pentafluorophenyl)borate or tetrakis(3,5-bistrifluormethylphenyl)borate.

5. Process according to claim 1, wherein the resulting olefin polymer has a molecular weight distribution Mw/Mn of 1.5 to 2.5.

6. Process according to claim 1, wherein in the metal complex Z represents a silsesquioxane ligand having the formula $(RSiO_{1.5})_7O_{1.5}$, $(RSiO_{1.5})_7O_{1.5}B$, or $(RSiO_{1.5})_7O_{1.5}B_2$.

7. Process according to claim 1, wherein Z represents a silsesquioxane having the formula $(RSiO_{1.5})_7O_{1.5}$.

8. Process according to claim 1, wherein the metal complex has the formula:

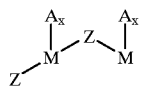

or

9. Process according to claim 1, wherein the metal complex has the formula:

10. Process according to claim 1, wherein the metal complex is supported on a carrier.

11. Process according to claim 10, wherein the carrier is silica.

12. Process according to claim 1, wherein the metal complex is represented by the formula:

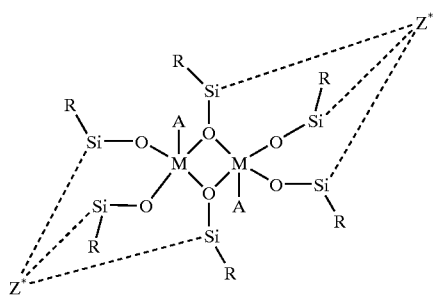

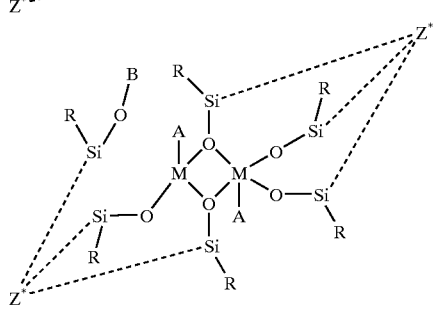

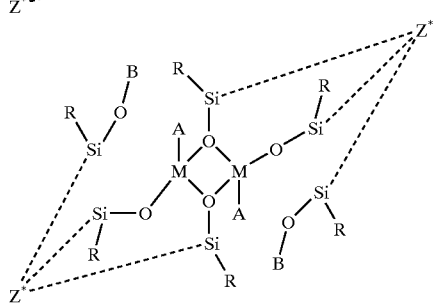

-continued
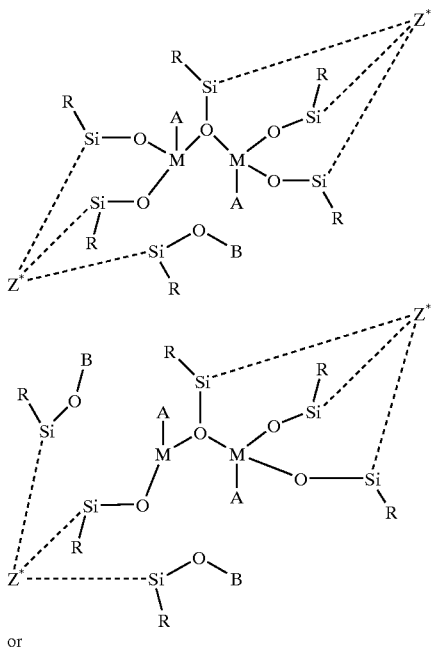
or
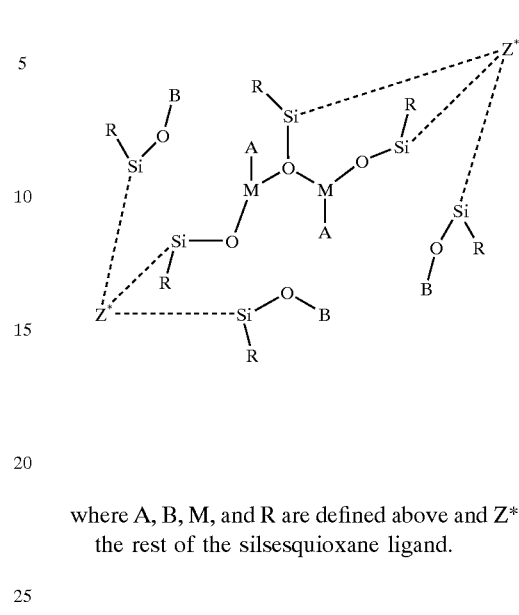
where A, B, M, and R are defined above and Z* represents the rest of the silsesquioxane ligand.
* * * * *